United States Patent [19]

Castleman

[11] Patent Number: 4,878,912
[45] Date of Patent: Nov. 7, 1989

[54] FOLDABLE INTRAOCULAR DISC LENS

[76] Inventor: Lawrence D. Castleman, 1201 Water Cliff Dr., Bloomfield Hills, Mich. 48013

[21] Appl. No.: 269,189
[22] Filed: Nov. 9, 1988
[51] Int. Cl.$^4$ .............................................. A61F 2/16
[52] U.S. Cl. ...................................................... 623/6
[58] Field of Search ......................................... 623/6

[56] References Cited

U.S. PATENT DOCUMENTS

| | | | |
|---|---|---|---|
| 4,485,499 | 12/1984 | Castleman | 623/6 |
| 4,562,600 | 1/1986 | Ginsberg et al. | 623/6 |
| 4,704,122 | 11/1987 | Portnoy | 623/6 |
| 4,769,034 | 9/1988 | Poley | 623/6 |
| 4,781,717 | 11/1988 | Grendahl | 623/6 |

FOREIGN PATENT DOCUMENTS 2124500A  2/1984  United Kingdom ..................... 623/6

OTHER PUBLICATIONS

"Intercapsular Implantation of Various Posterior Chamber IOLs; Animal Test Results" by D. J. Apple et al., Reprint from Opththalmic Practice, vol. 5, No. 3, Sep. 1987, pp. 100-104 and 132-134.

Model SI-18B Phacoflex, Posterior Chamber Silicone IOL, Allergan Medical Optics, Division of Allergan, Inc., P.O. Box 2515, Santa Ana, Calif., 4 page, Investigational Brochure Sheet's.

Primary Examiner—Ronald L. Frinks
Attorney, Agent, or Firm—Krass & Young

[57] ABSTRACT

An intraocular disc lens is provided that is fully foldable and unfoldable for intercapsular plantation in the aphakic capsular sac. The lens when thus folded is well suited for insertion through an incision such as an endophakeoemulsification incision and for unfolding with autocentration in the sac. The lens includes a posterior capsule supporting ridge for purposes of postoperative corrective laser surgery and/or barrier protection against unwanted invasive cell growth into the visual axis.

20 Claims, 4 Drawing Sheets

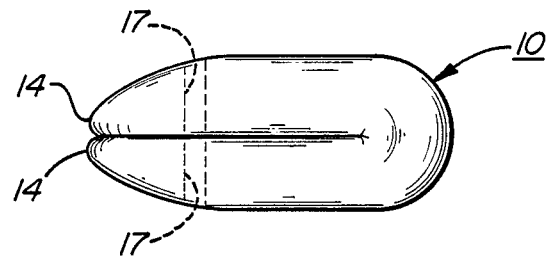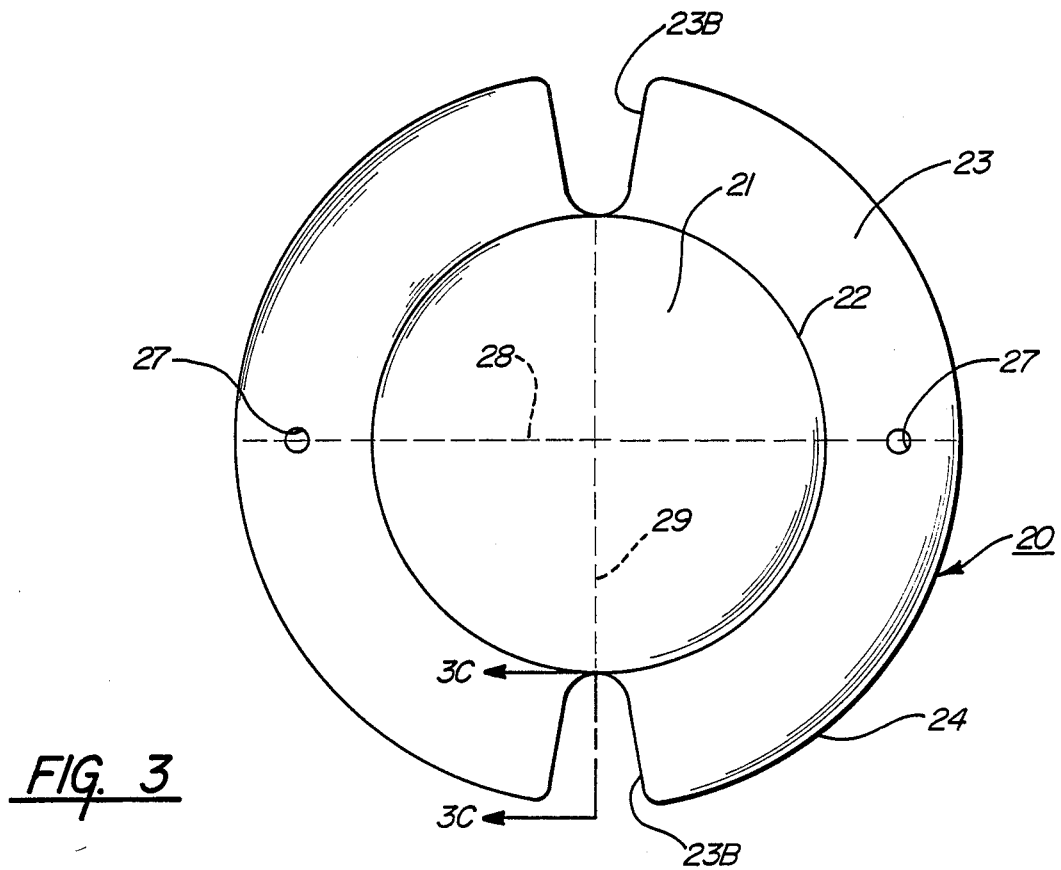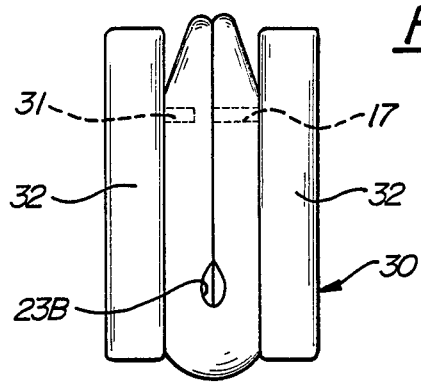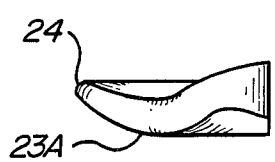

FOLDABLE INTRAOCULAR DISC LENS

FIELD OF THE INVENTION

This invention concerns the practice of medicine and more particularly a unique kind of intraocular lens (IOL). The lens is a flexible intraocular polymeric disc lens that is foldable for surgical insertion and intercapsular implantation in the aphakic capsular sac.

BACKGROUND ART

Animal test results have been reported by Apple et al. (*Opthalmic Practice*, 5:100,1987) for intercapsular implantation of various posterior chamber IOLs. These lenses included several styles with circular or disc configuration such as flexible disc lenses but did not include lenses with an optic having the ability to be folded.

One diametrically opposed J-loop haptic lens style for investigational use for capsular bag fixation features a flexible silicone polymer lens optic that is partly folded for insertion. Folding is done by wrapping the lens half-way around a rod-like tool placed across the lens diameter in parallel with the diametrically opposed haptic loops (Model SI-18, available from Allergan Medical Optics, Santa Ana, CA). Thus, folding of the haptic lens style is partial and is limited for purposes of insertion to such folding on a line conforming with the alignment of the haptic loops.

It therefore is an object of the present invention to provide an improved intraocular lens that is a fully foldable and unfoldable disc lens for purposes of intercapsular implantation and autocentration.

It also is an object of the present invention to provide an intraocular lens of the kind described that when implanted includes a behind-the-lens confined zone or cavity for post operative laser surgical intervention on the visual axis between the lens and the posterior capsule.

It is a further object of the invention to provide an intraocular lens that when implanted includes behind-the-lens open space confined by the posterior capsule and by barrier means to unwanted invasive post operative growth into the open space.

These and other objects, features and advantages will be seen from the following summary and detailed description of the invention.

SUMMARY AND DETAILED DESCRIPTION OF THE INVENTION

The invention in one preferred embodiment concerns a flexible and fully foldable intraocular polymeric disc lens for intercapsular insertion into a surgical incision of an aphakic capsular sac. After it is inserted, the disc lens is unfoldable within the sac to a substantially flat form for vision-enabling implantation within the sac in normal lens-oriented relation parallel to the iris plane. The disc lens is in the form of a substantially circular disc body having an anterior face and a posterior face. The disc body includes a central optic portion and a unitary rim that is circumferentially co-extensive with the inner lateral dimensions of the capsular sac so as to afford autocentration of the lens when implanted. The posterior surface of the rim is axially spaced apart from the posterior surface of the optic portion so that when the disc lens is implanted in the sac the rim posterior surface contacts the posterior capsule of the sac and the posterior optic surface is axially spaced away from the posterior capsule. The spaced apart surface of the rim thus provides a behind-the-lens cavity within the rim as a site for postoperative corrective laser surgery behind the lens. In another embodiment, a circumferential portion of the posterior rim surface is axially spaced apart from the posterior optic surface and serves as a continuous circumferential barrier ridge to cell growth or migration of cells. Thus, when the disc lens is implanted in the sac, the ridge contacts the posterior capsule in barrier fashion whereas the posterior optic surface is meanwhile axially spaced away from the posterior capsule so that an open zone or confined open space is created behind the lens into which space invasive growth of cells is inhibited by means of the surrounding barrier.

Preferably, the posterior surface of the rim of the unfolded disc body extends forwardly at an angle with respect to the plane of the central optic portion, preferably at an angle ranging from about 6 to about 8 degrees, such that said surface is in co-extensive circumferential contact with the similar forwardly angulated inner surface of the posterior capsule when the disc lens is centrally implanted.

In a preferred embodiment, the disc lens includes manipulation means comprising an axially perforate rim, preferably with diametrically opposed rim perforations which may be partial or full depth perforations. The disc lens preferably is foldable on a fold line across one face thereof at right angles to an opposed pair of perforations whereby the disc lens can be held in folded relation by insertion tool means adapted to engage with said perforations.

In one preferred embodiment the disc lens is foldable on a fold line across one face such as the anterior face so that the face of the disc lens can be fully folded upon itself to the fold line in face-to-face relation, i.e. with fully co-extensive facial contact. This complete or full folding serves to make the disc body more compact when thus folded, for purposes of more facile insertion into and through the capsulotomy. In another preferred embodiment, the edges of the rim intersected by the fold line are configured as opposed indentations or notches so that the fold location and the folding of the lens are facilitated.

In another aspect, the invention concerns a method of implanting a flexible polymeric intraocular disc lens dimensioned for autocentration. The method comprises the steps of fully folding the disc body upon itself in face-to-face relation as described, placing the thus folded disc body into the sac by insertion through a capsular incision, unfolding the folded disc body within the sac, and centering the unfolded disc body in normal lens-oriented relation parallel to the iris plane. Preferably the folding is done on an imaginary or established fold line such as the diameter across one face, e.g. the anterior face. Preferably, folding is accomplished by hand tool means adapted to engage and bring together opposite rim edges of the disc body located at right angles to the fold line such that the disc lens becomes fully folded for insertion.

BRIEF DESCRIPTION OF THE DRAWINGS

The invention will be more fully understood by reference to the accompanying drawings and the following description in which drawings:

FIG. 2C is a side view of the disc lens of FIG. 2 fully folded upon itself at the front face in face-to-face relation;

FIGS. 3 and 4 are each a plan view similar to FIG. 1 of a preferred disc lens that has diametrically opposed disc rim notches;

FIG. 3A is a side view of the disc lens of FIG. 3 being held by implant forceps in the fully folded position;

FIGS. 3C and 4A are sectional views taken respectively on lines 3C—3C and 4A—4A of FIGS. 3 and 4;

DESCRIPTION OF PREFERRED EMBODIMENTS AND BEST MODE OF PRACTICING THE INVENTION

The following description concerns preferred embodiments of the invention for purposes of illustrating the invention. Thus, this description is to be read broadly and not to be taken in a limited sense.

Figure 1:
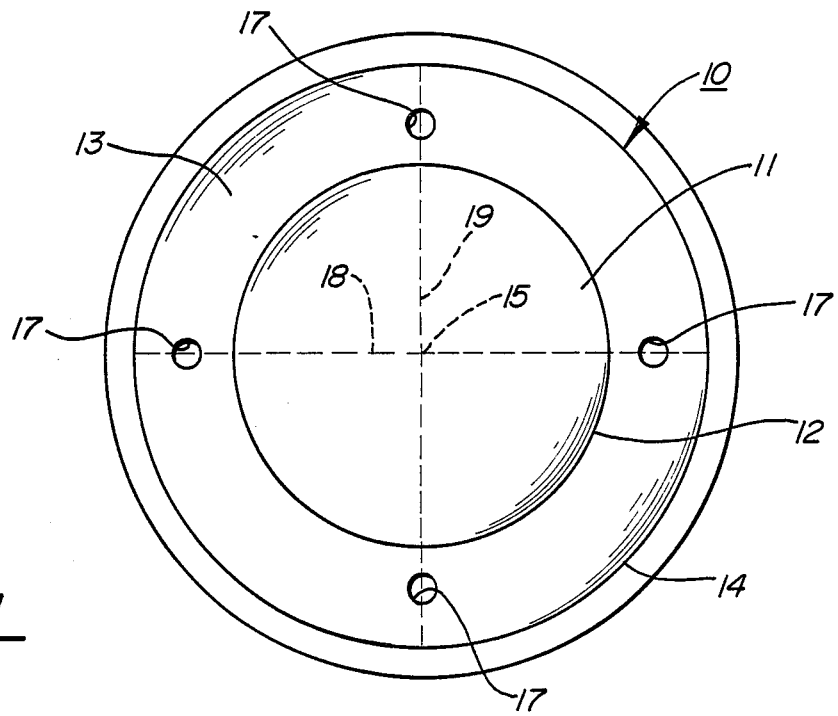
FIG. 1 is a plan view of the anterior surface of a preferred disc lens implanted with centration in contact with the capsular sac.

Referring to FIG. 1, the disc lens 10 which in situ is dimensionally stable includes a lens optic 11, an optic margin 12 and a unitary non-optic lens rim 13. The edge 14 of the rim serves to provide the lens with a position of autocentration within the capsular sac at the visual axis or centration point 15 by its circumferential contact with the circumferential, evenly lens-supported inner surface of the capsular sac. The plane 16 of the lens (FIG. 2A) is parallel to the iris plane (not shown). Axial guide holes 17 or recesses are provided in diametrically opposed alignment with the horizontal and vertical opposed diameters 18,19. As shown in FIG. 2A, with respect to the lens plane 16, the plane 16 of the lens rim is angulated first rearwardly from the optic margin 12 to a circular rim ridge 13A and then forwardly to the rim 'edge 14. The posterior surface of the ridge 13A and lens rim 13 thus provides an annular support surface 13B for the inner surface of the posterior capsule, for purposes to be described presently. When the lens is implanted in the capsular sac as seen in FIG. 2B, the posterior and anterior capsule inner surfaces conform closely to the support surface 13B, the rim edge 14 and the anterior surface 10A, and a behind-the-lens vault space IIB is left within the circumferential ridge 13A. At the front of the lens, after capsulorhexis, i.e. removal of circular section of the anterior lens capsule, a capsulorhexis margin is left as illustrated in FIG. 2B.

Figure 5:
FIGS. 5 and 6 are each a side view in elevation of a disc lens similar to that of FIG. 1.
Figure 5A:
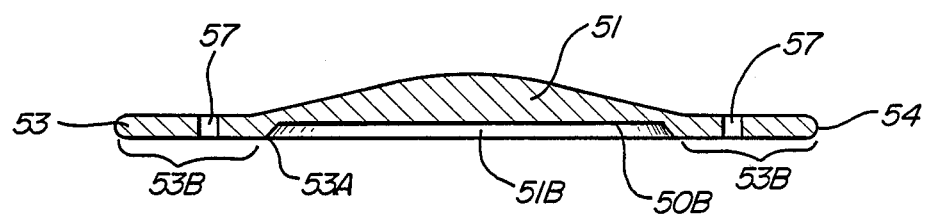
FIGS. 5A and 6A are cross-sectional views each taken on a diameter of the disc lenses of FIGS. 5 and 6 respectively.
Figure 6:
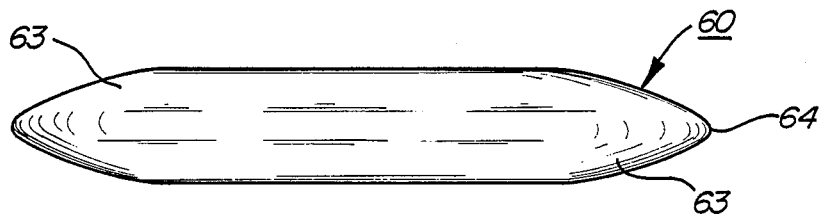
Figure 6A:
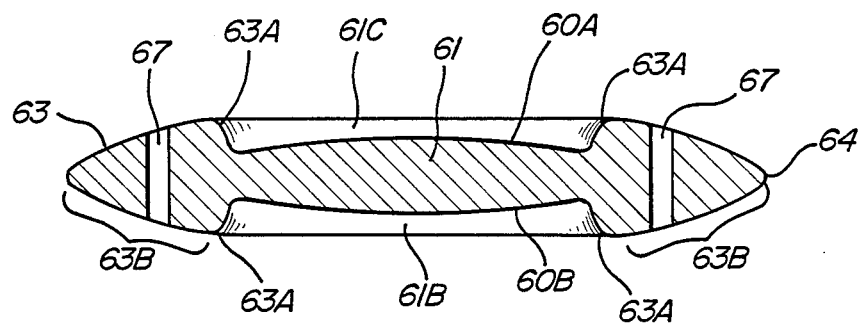

Other preferred embodiments featuring a behind-the-lens vault space are shown in FIGS. 5 and 6. These disc lenses 50,60 include respectively a lens optic 51,61, a lens rim 53,63, guide recesses 57,67, posterior capsule support surfaces 53B,63B and behind-the-lens vault spaces 51B,61B. The disc lens 60 of FIGS. 6 and 6A also includes an anterior vault space 61C which serves within the ridge 63A to delineate the frontal aspect of the lens optic 61 and to provide an additional open zone for post operative corrective laser surgery.

In a preferred embodiment as shown in FIG. 3, the disc lens 20 includes a lens rim 23 with opposed notches having a curvilinear margin 23B located at the ends of a lens diameter fold line 29. The notches serve to locate the fold line which is at right angles to a lens diameter 28 between opposed guide holes 27. These guide holes serve to provide lens gripping access for a tool such as the indexing fingers 31 of the blades 32 of an implant forceps tool 30 (FIG. 3A). A similar preferred embodiment is shown in FIG. 4 where the lens 40 includes lens rim 43 that has opposed notches having a curvilinear margin 43B for locating the fold line and facilitating folding by decreasing the fold width. As shown in FIG. 4A, the lens features a ridge 43A axially spaced apart from the posterior optic surface 41A thus providing a behind-the-lens vault space 41B.

Figure 2:
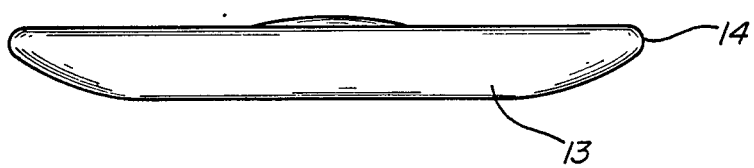
FIG. 2 is a side view in elevation of the disc lens shown in FIG. 1.
Figure 2A:
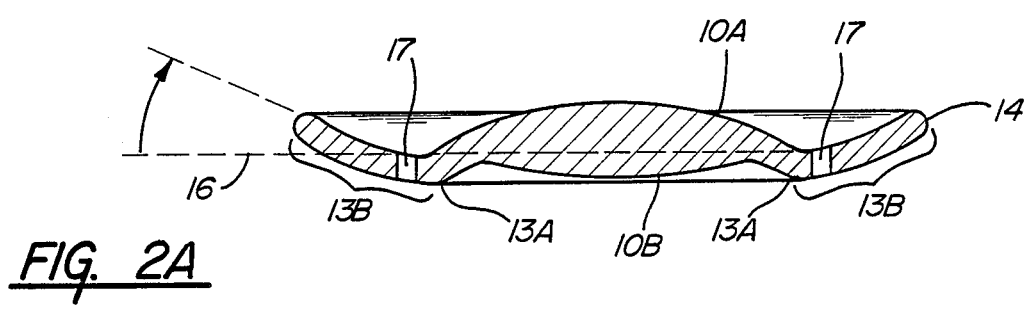
FIG. 2A is a cross-sectional view taken on a diameter of the lens of FIG. 2.
Figure 2B:
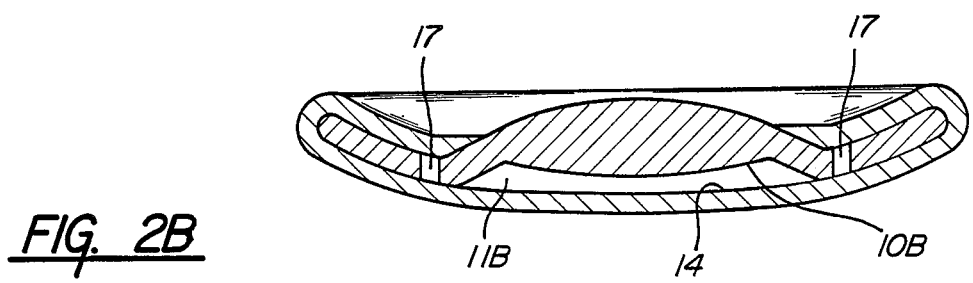
FIG. 2B is a similar view shown in a position of autocentration within a capsular sac.
Figure 3B:
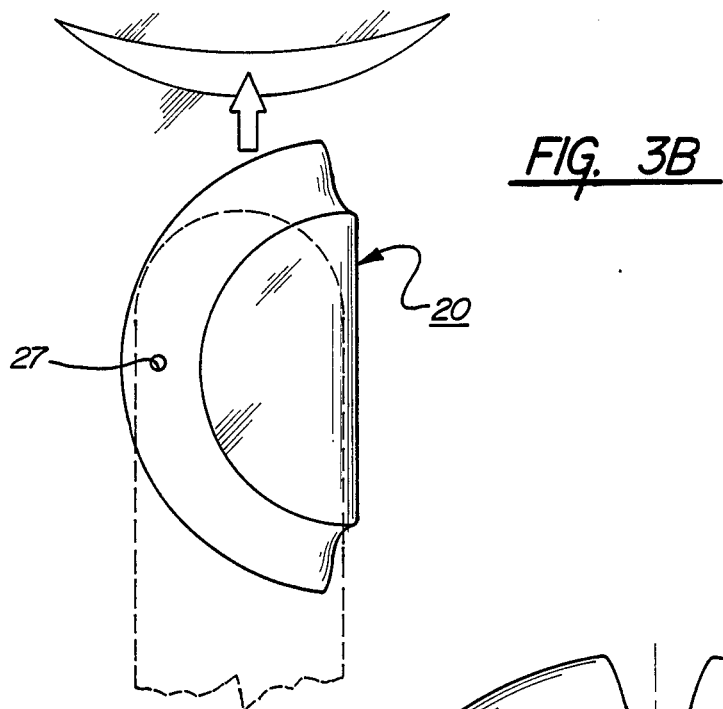
FIG. 3B is a plan view of the forceps-held fully folded disc lens in a preferred form showing the positioning of the lens for insertion within the capsular sac via an anterior capsulotomy.
Figure 4:
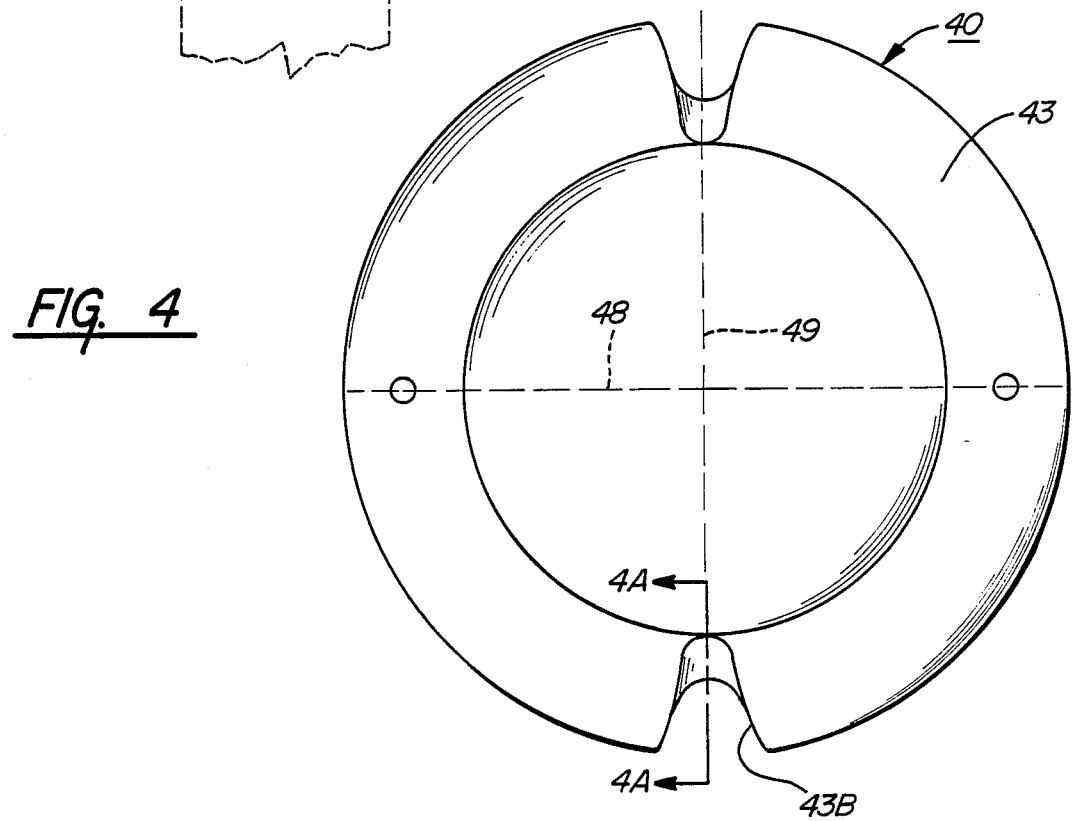
Figure 4A:
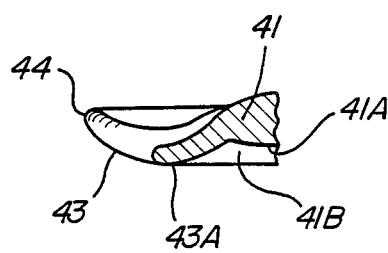

Folding of the lens is illustrated in FIG. 2C, 3A, and 3B. FIG. 2C shows the full folding of the disc lens of FIG. 1 on the vertical diameter fold line 19 achieved by manipulating, aligning and bringing together the guide recesses 17 on the horizontal diameter 18 to the full folded position shown. FIG. 3A also shows the full folding on the diameter fold line 29 of the dual-notch disc lens 20 of FIG. 3. Folding is accomplished by engaging the tool finger recesses 27 (FIG. 3A) with the opposed blade indexing fingers 31 of the blades 32 of an open implant forceps tool and closing the forceps blades sufficiently to achieve full folding. FIG. 3B shows schematically the manner of positioning the fully folded-disc lens 20 with forceps (one forceps blade 32 of FIG. 3A being partly shown and being in dotted outline) for insertion of the lens within the anterior capsulotomy.

The disc lens of the invention can be made of any suitable medical grade soft foldable and flexible solid intraoptical quality biocompatible elastomer such as an IOL optical quality silicone elastomer that after folding and unfolding returns to original optical resolution within a short period. The disc lens can be made as a single unitary article by injection molding or other conventional plastic optic lens molding methods. The lens optic may have any suitably prescribed correction and preferably will have a conventional shape such as a biconvex shape. Typically, the optic is circular and has a diameter of about 6 mm. and a maximum thickness of about 0.5 to about 1 mm. The preferred average axial depth centrally of the vault space is about 0.05 to about 0.1 mm. with respect to the ridge plane (e.g. as in FIGS. 2A and 6A).

What is desired to claim as my exclusive property in the invention, as described, is the following.

1. A flexible intraocular polymeric disc lens that is foldable for intercapsular insertion into a surgical incision of an aphakic capsular sac and is unfoldable within the sac for vision-enabling implantation therein in normal lens-oriented relation parallel to the iris plane, comprising:

a substantially circular disc body having an anterior face and a posterior face, the disc body including a central optic portion and a unitary forwardly dished rim that is circumferentially coextensive with the inner lateral dimensions of said sac so as to afford autocentration of the lens when implanted, the posterior surface of said rim of the unfolded disk body being extended forwardly at a rim angle with respect to the plane of the central optic portion and being axially spaced apart from the posterior surface of said optic portion such that when the disc lens is folded, implanted centrally in the sac and unfolded the rim posterior surface is in coextensive annular contact with the similar forwardly angulated inner surface of the posterior capsule of the sac and the posterior optic surface is axially spaced away from the posterior capsule thereby providing a behind-the-lens cavity within the rim as a site for postoperative corrective laser surgery behind the lens.

2. A disc lens according to claim 1 where said angle is in the range from about 6 to about 8 degrees.

3. A disc lens according to claim 1 with lens manipulation means comprising an axially perforate rim.

4. A disc lens according to claim 3 where the manipulation means comprises diametrically opposed rim perforations.

5. A disc lens according to claim 4 that is foldable on a fold line across one face thereof where the opposed pair of perforations is aligned at right angles to said fold line whereby the disc lens can be held in folded relation by insertion tool means adapted to engage with said perforations.

6. A disc lens according to claim 4 where said perforations are partial or full depth perforations.

7. A disc lens according to claim 1 that is foldable on a fold line across one face thereof, the optic portion being void-free and the edges of the rim intersected by the fold line being notched such that the fold location and the folding of the lens are facilitated.

8. A flexible intraocular polymeric disc lens that is foldable for intercapsular insertion into and through a surgical incision of an aphakic capsular sac and is unfoldable within the sac for vision-enabling implantation within the sac in normal lens-oriented relation parallel to the iris plane, comprising:

an axially symmetrical substantially circular disc body having an anterior face and a posterior face, the disc body including a generally planar void-free lens optic, an optic margin, and a unitary forwardly dished non-optic rim that is laterally co-extensive with the sac and being foldable on a fold line across one face thereof so that said face can be fully folded upon itself to the fold line in face-to-face contacting relation thereby making the disc body more compact when thus folded for purposes of envelope insertion into and through said incision, the posterior surface of the lens rim with respect to the lens plane being extended first rearwardly at an angle from the lens optic to a circumferential rim ridge and then forwardly to the rim edges such that when the lens is folded, implanted centrally in the sac and unfolded, the rim posterior surface is in co-extensive annular contact with the similar forwardly angulated inner surface of the posterior capsule.

9. A disc lens according to claim 8 having an opposed pair of perforations aligned at right angles to said fold line whereby the disc lens can be held in folded relation by insertion tool means adapted to engage with said perforations.

10. A disc lens according to claim 9 where said perforations are partial or full depth perforations.

11. A disc lens according to claim 8 that is foldable on a fold line across one face thereof, the edges of the rim intersected by the fold line being notched such that the fold location and the folding of the lens are facilitated.

12. A method of implanting an intraocular lens according to claim 9 comprising the steps of fully folding the disc body upon itself in face-to-face contacting relation such that the disc body is made more compact for purposes of insertion into a surgical incision of an aphakic capsular sac, placing the thus folded disc body into the sac by envelope insertion through the incision, unfolding the folded disc body within the sac and centering the thus sac coextensive unfolded disc body in normal lens-oriented relation parallel to the iris plane for vision-enabling intercapsular implantation.

13. A flexible intraocular polymeric disc lens that is foldable for intercapsular insertion into a surgical incision of an aphakic capsular sac and is unfoldable within the sac for vision-enabling implantation within the sac in normal lens-oriented relation parallel to the iris plane, comprising:

a substantially circular disc body having an anterior face and a posterior face, the disc body including a generally planar central void-free optic portion and a unitary forwardly dished rim that is circumferentially co-extensive with the inner lateral dimensions of said sac so as to afford autocentration of the lens when implanted, a circumferential portion of the posterior surface of said rim being axially spaced apart from the posterior surface of said optic portion and serving as a continuous circumferential barrier ridge such that when the disc lens is implanted in the sac the ridge contacts the posterior capsule of the sac and the posterior optic surface is axially spaced away from the posterior capsule thereby providing a barrier to invasive growth of cells into the confined open space behind the lens.

14. A disc lens according to claim 13, where the posterior surface of the rim of the unfolded disc body extends forwardly at an angle with respect to the plane of the central optic portion such that said surface is in co-extensive circumferential contact with the posterior capsule when the disc lens is centrally implanted.

15. A disc lens according to claim 14, where said angle is in the range from about 6 to about 8 degrees.

16. A disc lens according to claim 14, where lens manipulation means comprising an axially perforate rim.

17. A disc lens according to claim 16, where the manipulation means comprises diametrically opposed rim perforations.

18. A disc lens according to claim 17, that is foldable on a fold line across one face thereof where the opposed pair of perforations is aligned at right angles to said fold line whereby the disc lens can be held in folded relation by insertion tool means adapted to engage with said perforations.

19. A disc lens according to claim 17, where said perforations are partial or full depth perforations.

20. A flexible intraocular polymeric disc lens that is foldable for intercapsular insertion into a surgical incision of an aphakic capsular sac and is unfoldable within the sac for vision-enabling implantation within the sac in normal lens-oriented relation parallel to the iris plane, comprising:

a substantially circular disc body having an anterior face and a posterior face, the disc body including a central optic portion and a unitary rim that is circumferentially co-extensive with the inner lateral dimensions of said sac so as to afford autocentration of the lens when implanted, circumferential portions of the anterior and posterior surfaces of said rim being axially spaced apart from the respective anterior and posterior surfaces of said optic portion and serving respectively as anterior and posterior circumferential barrier ridges such that when the disc lens is implanted in the sac the ridges contact the anterior and posterior capsule of the sac and the respective anterior and posterior optic surfaces are axially spaced away from the anterior and posterior capsule surfaces thereby defining a ridge confined open space both in front of the lens and behind the lens.

* * * * *